United States Patent [19]
Pennington et al.

[11] Patent Number: 5,942,525
[45] Date of Patent: *Aug. 24, 1999

[54] SPOT TREATMENT OF ANIMALS WITH PYRIPROXYFEN AND AN INSECTICIDE

[75] Inventors: Robert G. Pennington, Rayville; James V. Grissom, Lawson; Joseph E. Dyer, Kansas City, all of Mo.

[73] Assignee: Ecto Development Corporation, Excelsior Springs, Mo.

[ * ] Notice: This patent issued on a continued prosecution application filed under 37 CFR 1.53(d), and is subject to the twenty year patent term provisions of 35 U.S.C. 154(a)(2).

[21] Appl. No.: 08/796,593

[22] Filed: Feb. 7, 1997

Related U.S. Application Data

[63] Continuation of application No. 08/438,950, May 11, 1995, abandoned.

[51] Int. Cl.$^6$ .................. A01N 43/40; A01N 53/00
[52] U.S. Cl. ................................ 514/345; 514/531
[58] Field of Search .................... 514/345, 521, 514/531

[56] References Cited

U.S. PATENT DOCUMENTS

| | | | |
|---|---|---|---|
| 4,178,384 | 12/1979 | Ensing | 424/305 |
| 4,764,529 | 8/1988 | Naik et al. | 514/531 |
| 4,780,459 | 10/1988 | Matthewson | 514/136 |
| 4,826,874 | 5/1989 | Bonin et al. | 514/521 |
| 4,879,292 | 11/1989 | Nishida et al. | 514/241 |
| 5,057,527 | 10/1991 | Alig et al. | 514/345 |
| 5,236,954 | 8/1993 | Gladney et al. | 514/531 |
| 5,266,324 | 11/1993 | Stendel et al. | 424/411 |
| 5,286,749 | 2/1994 | Kieran et al. | 514/531 |
| 5,310,557 | 5/1994 | Brandt et al. | 424/411 |

FOREIGN PATENT DOCUMENTS 0 576 267 A1  6/1993  European Pat. Off. .

OTHER PUBLICATIONS

Introduction of Vitellogenin Synthese in *Locusta migratoria* by the Juvenile Hormone Analog, Pyriproxyfen, Gordon C. Edwards, Ralph P. Braun, and Gerard R. Wyatt, published in the J. Insect Physiol, vol. 39,No. 7, pp. 609–614, 1993.

Worthing et al, The Pesticide Manual, $9^{th}$ Ed. (1991) pp. 662–663.

*Primary Examiner*—Allen J. Robinson
*Attorney, Agent, or Firm*—Litman, Kraai & Brown, L.L.C.

[57] ABSTRACT

A method for treating animals to rid the animal's body of ectoparasites such as fleas and ticks comprising applying a spot treatment of a composition to the exterior surface of the animal's body containing a growth regulating effective amount of pyriproxyfen or derivatives thereof and an insecticide.

5 Claims, No Drawings

SPOT TREATMENT OF ANIMALS WITH PYRIPROXYFEN AND AN INSECTICIDE

CROSS REFERENCE TO RELATED APPLICATION

The present application is a continuation of U.S. application for patent Ser. No. 08/438,950 filed May 11, 1995 on SPOT TREATMENT OF ANIMALS WITH PYRIPROXYFEN AND INSECTICE, now abandoned.

BACKGROUND OF THE INVENTION

This invention relates to the general field of controlling insect pests with chemical agents and in particular to the spot treatment of animals with an insect growth regulator.

Parasitic infestation by fleas, ticks and the like of domestic animals, such as dogs and cats, results in considerable nuisance, pain and possible harm to the infested animals as well as the animals' owners. Such infestation also results in the transmission of disease to and between humans and domestic animals. For this reason effective control of such parasites has always been desirable and necessary.

Adult fleas generally live in the coat and surrounding environment of the host animal. They feed on the host's blood and lay their eggs in the host's coat. Many of the flea eggs do not stick to the animal, because they are not glued to the coat or skin, and so the eggs fall off the animal into the surrounding environment. Insecticides applied to the animal will generally kill the adult fleas on the animal, but are not generally effective in killing the egg or pupated stages of the fleas because these stages are not normally on the animal. Except where an insecticide has an extremely long effective or residual life, use of such insecticides generally does not prevent re-infestation at the time when the eggs released by fleas prior to or during treatment subsequently hatch, mature through a pupa stage and return to the animal as adults.

Active compounds which inhibit the growth of parasites, such as fleas, have been developed and are applied to the host animal. It is believed by applicants that these compounds either contaminate the eggs or are incorporated into the eggs and thereby effect growth of the eggs and pupae and also thereby prevent eggs and pupated stages of the parasites from developing into adults. In this manner the fleas are prevented from subsequently breeding and re-infestation. Pyriproxyfen or 2-1-methyl-2-(4-phenoxyphenoxy) ethoxy pyridine is a known insect growth regulator, as are insect growth regulators (IGRs) such as lufenuron, diflubenzuron, methoprene and fenoxycarb. U.S. Pat. No. 5,266,324 discloses use of pyriproxyfen in collars for domesticated animals. Applicant understands that formulations containing pyriproxyfen at concentrations of approximately 0.125% by weight have been applied to dogs and cats as a whole body spray or dip to prevent the hatching or maturation of flea eggs and larvae.

Application methods other than collars are desirable because many pet owners consider the collars unsightly and ineffective. Further, such collars often annoy the pets to which they are secured. Application of the active compound through dips or sprays is often undesirable in that such treatments, particularly dips, are difficult to administer and often result in considerable stress to the treated animals. Further, such applications require relatively large amounts of solvent and in the case of dips often result in the waste of considerable excess material.

SUMMARY OF THE INVENTION

The present invention is directed to a method for treating animals to rid the animal's body of ectoparasites and to prevent eggs that are laid by the parasites from maturing into adults even when the eggs fall off the animal that has been treated. The method comprises applying to a selected portion of the exterior surface of the animal's body, especially a single or dual spot dosage, a composition containing a growth regulating effective amount of pyriproxyfen or derivatives thereof, so as to provide sustained control of parasites for approximately 90 to 120 days by killing parasite eggs directly, by preventing eggs from developing into larvae or pupae and/or by preventing pupae from maturing into adults. In a preferred embodiment of the invention a general insecticide, especially a pyrethroid, is incorporated in the composition to kill parasitic adult stages of the ectoparasites especially those present on the animal at time of treatment or those that transfer to the animal from another source. The present invention has been found to be especially effective against ectoparasitic insects such as fleas and certain arachnids such as ticks.

OBJECTS AND ADVANTAGES OF THE INVENTION

Therefore, it is an object of this invention to provide a method for controlling parasite insects such as fleas and arachnids such as ticks from animals; to provide such a method comprising the spot application of a growth regulating effective amount of pyriproxyfen to the infected animal; to provide such a method which further comprises the spot application of an insecticidal effective quantity of a pyrethroid in combination with the pyriproxyfen; to provide such a method which is convenient to apply and reduces the stress on the animal treated; to provide such a method that does not require use of a collar or other fixed carrier; to provide such a method that provides sustained and long lasting parasite control for approximately 90 to 120 days; and to provide such a method which is relatively inexpensive and particularly well adapted for its intend purpose thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific composition and functional details disclosed herein are not to be interpreted as limiting, but merely as a basis for the claims and as a representative basis for teaching one skilled in the art to variously employ the present invention in virtually any appropriately detailed structure.

For the purpose of this application the term ectoparasites should be deemed to include parasitic insects such as fleas and mosquitos, parasitic arachnids such as ticks and related pests and parasites of warm-blooded animals.

The present invention is directed to a method for treating animals, especially mammals such as dogs, cats and livestock, to control parasitic insects such as fleas and arachnids such as ticks and other insect pests through the application of a formulation comprising an insect growth regulating effective concentration of pyriproxyfen and the composition itself. Pyriproxyfen 2-(1-methyl-2-(4-phenoxyphenoxy)-ethoxy)-pyridine has a chemical formula of:

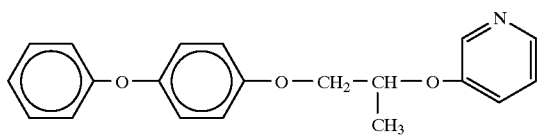

It is foreseen that the formulation may comprise insect growth regulating effective salts or other related derivatives of pyriproxyfen. It is also foreseen that other insect growth regulators, juvenile hormone analogs or chitin inhibitors which kill parasite eggs, prevent eggs from developing into larvae, prevent larvae from developing into pupae, prevent pupae from developing into adults, prevent development of nymph stages or development of nymphs into adults or otherwise prevent the development of mature parasites may be utilized as alternatives to pyriproxyfen. Such alternatives include fenoxycarb, ethyl(2-(4-phenoxyphenoxy)ethyl) carbamate, methoprene, lufenuron and diflubenzuron. Fenoxycarb Technical, comprising 96% fenoxycarb, is manufactured by Ciba-Geigy Corporation and diflubenzuron is available under the trademark Demilin.

The method preferably involves applying the pyriproxyfen in combination with an insecticide to kill adult insect parasites. Preferably, the insecticide is an insecticidal pyrethroid such as permethrin, 3-(phenoxyphenyl) methyl(±)-cis, trans-3-(2,2 dicloroethenyl)-2,2 dimethylcyclopropanecarboxylate, having a formula of:

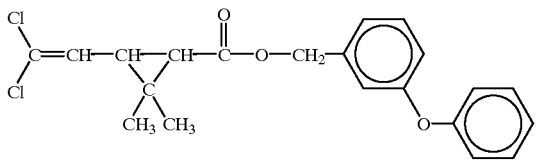

It is foreseen that the following pyrethroids, as more fully disclosed in U.S. Pat. No. 5,286,749 (which is incorporated herein by reference), would be suitable for use: phenothrin, deltamethrin, cypermethrin, cyhalothrin, flumethrin, cyfluthrin, cyphenothrin, tralomethrin, tralocythrin and fenvalerate. It is foreseen that non-pyrethroid compositions that will kill the parasitic stages of the ectoparasites without harming the mammal may be alternatively used in accordance with the invention.

The preferred formulation comprises approximately 45% by weight permethrin and 5% by weight pyriproxyfen. The preferred formulation may be formed by combining: approximately 50% by weight Permethrin Technical Insecticide, from Zeneca Ag Products, which comprises approximately 91% by weight permethrin; approximately 10% by weight of a commercially available product which is sold under the trademark Nylar and which comprises approximately 50% by weight pyriproxyfen and approximately 50% by weight corn oil; approximately 10% by weight mineral oil such as is sold under the trademark Duopac 70 from Lyondell Petrochemical Co.; and approximately 30% by weight D-Limonene technical which is sold by Florida Chemical Co., Inc.

The corn oil in the Nylar product functions as a solvent for the pyriproxyfen. While applicant does not intend to be bound to a specific theory of operation, it is believed in the present invention that the mineral oil functions as a solvent for the pyriproxyfen and the permethrin and also reduces the viscosity of the overall composition. Additional preferred concentrations of mineral oil range from approximately 1% to 30% by weight of the total composition. While the D-Limonene may have other functions, it is incorporated primarily as a fragrance and provides a citrus scent. Additional preferred concentrations of D-Limonene range from approximately 10% to 50% by weight of the total composition. Limonene or 1-Methyl-4 -(1-methylethenyl) cyclohexene or p-mentha-1,8-diene has the following chemical formula:

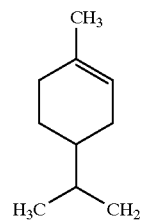

It is foreseen that any non irritating organic oils or petroleum distillates may be substituted for the mineral oil. Certain specific substitutes for the mineral oil include glycol ethers and water. Preferably, oils which are easily transdermally absorbed into mammalian internal systems, such as dimethyl sulfoxide (DMSO), should be avoided so as to avoid transfer of the composition actives systemically into the animals to be treated.

A pyriproxyfen composition in accordance with the invention may be applied to an animal in a water based solution, suspension or emulsion. Water based compositions of the invention are especially useful with cats.

The formulation in accordance with the invention is preferably applied to the animal to be treated through spot application or striping. The formulation is preferably applied at skin level. A preferred formulation, including 5% by weight pyriproxyfen and 45% by weight of permethrin ectoparasiticide, has been found to be effective in killing existing adult fleas and especially effective in preventing reinfestation of fleas by interfering with development of eggs or immature parasites into adult parasites for up to 120 days in dogs of up to 33 pounds, when applied as a single 1.5 ml dose at a single localized spot on the skin of the dog's back between the shoulder blades. An application of two 1.5 ml doses of formulation in localized spots, one between the shoulder blades and one directly in front of the base of the tail, has been found to be effective in treating dogs of over 33 pounds for up to 120 days. As used herein the term "spot" means a localized application which may be elongate as a stripe or other geometric shape or may be a multiple location application for larger animals, but does not include application to an entire animal or application to an object held near to or worn on such an animal.

The concentration of pyriproxyfen in the formulation may range from about 0.25% to about 50% by weight with or without an insecticide such as permethrin. The formulations with concentrations ranging from 0.25% to 50% and more, preferably from 1% to 10% by weight pyriproxyfen may be applied at one or more localized spots on the animal or as a localized stripe on the animal. The most preferred concentration of pyriproxyfen is about 5% by weight. The total amount of the formulation applied typically ranges from 0.25 ml to 150 ml depending on the size of the animal to be treated and the pyriproxyfen concentration of the formula.

The following examples are provided for the purpose of illustrating certain aspects of the invention and are not intended to limit the scope of the invention.

EXAMPLE I

Flea/Tick Treatment Efficacy Study

The efficacy of a treatment of dogs with a formulation in accordance with the present invention identified as Formulation A, having 45% by weight permethrin and 5% by weight pyriproxyfen, was studied in comparison to the efficacy of a treatment with a formulation comprising 65% by weight permethrin and no pyriproxyfen which is commercially available under the trademark ExSpot and identified as Formulation B and also in comparison to a control group of animals that were treated with nothing. The following groupings of test animals, three dogs per group, were used in the study:

Group A1: Dogs weighing less than 33 pounds and treated with one 1.5 ml spot application (shoulder) of the Formulation A in accordance with the present invention.

Group A2: Dogs weighing more than 33 pounds and treated with two 1.5 ml spot applications (shoulder and in front of tail) of the Formulation A.

Group B1: Dogs weighing less than 33 pounds and treated with one 1 ml spot application (shoulder) of Formulation B.

Group B2: Dogs weighing more than 33 pounds and treated with two 1 ml spot applications (shoulder and front of tail) of Formulation B.

Group C1: Dogs weighing less than 33 pounds and untreated.

Group C2: Dogs weighing more than 33 pounds and untreated.

Prior to infestation, all the dogs were combed to remove fleas and ticks were removed by hand. On Test Day—1, each dog was infested with approximately 100 unfed adult fleas and approximately 50 unfed adult ticks. On Test Day 0, the dogs were treated as follows: the dogs in Test Group A1 received a spot application comprising 1.5 ml of Formulation A applied at the skin level between the shoulder blades; the dogs in Test Group A2 received separate 1.5 ml doses of Formulation A at skin level between the shoulder blades and on the back directly above the head of the tail; the dogs in Test Group B1 received 1.0 ml of Formulation B at the skin level between the shoulder blades; the dogs in Test Group B2 received separate 1.0 ml doses of Formulation B between the shoulder blades and on the back directly above the head of the tail; and the dogs in Test Groups C1 and C2 were not treated.

Each dog was reinfested with approximately 100 unfed adult fleas and approximately 50 unfed adult ticks on Test Days 10, 17 and 24 (away from the sites of application for each formulation). On test days 1–3, 11–13, 18–20 and 25–27 hand body counts were conducted to determine the number of live fleas and ticks and formulation efficacies. On Test Days 45 and 90 each dog in Test Groups A1 and A2 and C1 and C2 was infested with approximately 150–200 unfed adult fleas (away from the sites of the formulation application).

Flea ova collections were made on the fourth day following each of these infestations. Approximately 100 ova (if available) were collected from each dog on these days. The ova were observed for larval hatch at approximately 72 hours post-collection. A flea growth medium was added to the dishes containing the larva and adult flea counts were made at 21, 28 and 35 days following collection to determine how many, if any, larva matured to adults. One dog from each of groups A1, A2, C1 and C2 was then infested again at Test Day 119 with follow-up ova collection on Test Day 122.

On test Days 4 and 27, hair samples were collected and mixed from multiple body sites (but not the sites of the formulation application) on one randomly selected dog from each test group A1, A2, B1, B2, C1 and C2. Enough hair was removed from each dog to fill a single glass test tube (20 mm ×150 mm). Each test tube was infested with approximately 15 deer tick nymphs. The mouths of the test tubes were secured with foam stoppers and the test tubes were held under high humidity conditions conducive to tick survival. Live/dead tick counts were conducted at approximately 24 and 48 hours following the test tube infestations.

The percent efficacy against adult fleas and ticks (See Table 1) was calculated after each body count as follows:

((Mean number of live fleas or ticks on untreated dogs—Mean number of live fleas or ticks on treated dogs)/Mean number of live fleas or ticks on untreated dogs)×100.

The percent of adult fleas that developed within 35 days from the actual number of ova seeded at each collection period was used to determine product efficacy (See Table 2) using the following formula:

((Percent of adult fleas in the "control" dishes—Percent of adult fleas in the "treated" dishes)/Percent of adult fleas in the "control" dishes)×100.

The percent efficacy against nymphal deer ticks (See Table 3) was calculated after each count as follows:

((Mean number of live ticks in tubes containing untreated dog hair—Mean number of live ticks in tubes containing treated dog hair)/Mean number of live ticks in tubes containing untreated dog hair)×100.

SUMMARY OF RESULTS FOR EXAMPLE 1

As shown in Table 1 below, Formulation A consistently demonstrated higher levels of efficacy against fleas on dogs weighing less than 33 pounds than did Formulation B. The only exception was on Test Day 3 when Formulation A was 90.9% effective against fleas and Formulation B was 95.5% effective. Formulation A demonstrated a longer period of high levels of efficacy against fleas than Formulation B. The efficacy of the Formulation A against fleas remained above 80% through Test Day 20, whereas the efficacy of Formulation B remained above 80% only through Test Day 13.

In general, both products were equally effective against fleas on dogs weighing more than 33 pounds. Formulation A demonstrated efficacies greater than 90% against fleas through Test Day 20 and was approximately 86% effective against fleas at Test Day 27. Formulation B demonstrated efficacies greater than 86% through Test Day 20 and was approximately 88% effective against fleas at Test Day 27.

In general, both products demonstrated excellent efficacy (100%) against ticks on the smaller dogs beginning on Test Day 11 and remained consistently high (96.8–100%) through Test Day 20. Both products demonstrated acceptable tick efficacy (approximately 80%) at Test Day 27 against ticks on the smaller dogs.

Similarly both products demonstrated excellent efficacies against ticks on the larger dogs beginning on Test Day 11. However, the efficacy of Formulation A against ticks on the larger dogs remained higher than the efficacy of Formulation B throughout the study. In particular the efficacy of Formulation A remained above 94% through Test Day 27 whereas the efficacy of Formulation B dropped to 87% and below beginning on Test Day 25.

As shown in TABLE 3, both products were highly effective against the deer tick nymph regardless of whether the hair used was removed from the smaller or larger dogs. The effect of the formulation with respect to tick nymphs when applied in accordance with the procedure was considered surprising.

As shown in TABLE 2, Formulation A demonstrated excellent ovicidal activity through Test Day 123. The ovicidal activity of Formulation A demonstrates perhaps the most important characteristic of the inventive formulations. In particular, the formulations of the invention kill the eggs of fleas and/or inhibit growth of the immature fleas and prevent the eggs and pupae from maturing into adults even when the eggs are removed from the dogs and even though the dogs were treated with only a spot treatment of the inventive formulations.

The number of mosquito landings on each animal in the first five minutes following their introduction into the cages were counted by two or three observers. The number of mosquito landings recorded was the average count of these observers.

Approximately two hours following exposure to mosquitoes, the dogs were removed from the cages, returned to their housing, and the number of live and dead mosquitoes in the cages were recorded. The mosquitoes were removed from the cages by aspiration and all mosquitoes, alive and dead, were immediately squashed to determine whether any had taken blood from any of the dogs.

On Test Days 5, 14, 21 and 28, the six dogs identified during the pretreatment phase of the study were again

TABLE 1

OVERALL PERCENT (%) EFFICACY AGAINST FLEAS AND TICKS

| TEST DAYS | GROUP A1 FLEAS | GROUP A1 TICKS | GROUP A2 FLEAS | GROUP A2 TICKS | GROUP B1 FLEAS | GROUP B1 TICKS | GROUP B2 FLEAS | GROUP B2 TICKS |
|---|---|---|---|---|---|---|---|---|
| 1 | 97.7 | 31.0 | 92.5 | 30.0 | 67.7 | 19.5 | 97.5 | 77.0 |
| 2 | 97.7 | 27.7 | 92.3 | 0.0 | 89.8 | 39.7 | 99.2 | 67.7 |
| 3 | 90.9 | 71.7 | 96.9 | 45.2 | 95.5 | 83.3 | 100 | 95.9 |
| 11 | 97.9 | 100 | 100 | 100 | 83.9 | 100 | 97.9 | 91.9 |
| 12 | 100 | 100 | 100 | 100 | 90.4 | 100 | 100 | 100 |
| 13 | 100 | 100 | 100 | 100 | 92.0 | 100 | 100 | 100 |
| 18 | 93.4 | 100 | 98.9 | 94.7 | 62.9 | 96.8 | 86.1 | 100 |
| 19 | 81.9 | 100 | 100 | 95.5 | 38.6 | 100 | 89.7 | 100 |
| 20 | 82.5 | 100 | 94.6 | 100 | 56.4 | 100 | 100 | 97.9 |
| 25 | 35.5 | 68.5 | 88.2 | 96.1 | 0.0 | 72.6 | 71.1 | 87.0 |
| 26 | 64.4 | 79.5 | 76.7 | 96.1 | 30.5 | 75.9 | 60.0 | 74.0 |
| 27 | 36.7 | 78.5 | 85.6 | 100 | 24.9 | 81.3 | 87.6 | 49.1 |

TABLE 2

OVERALL PERCENT (%) EFFICACY OF FORMULATION A AGAINST FLEA OVA

| TEST DAY | OVICIDAL EFFICACY |
|---|---|
| 49 | 100 |
| 94 | 99.5 |
| 123 | 91.5 |

TABLE 3

OVERALL PERCENT (%) EFFICACY AGAINST NYMPHAL DEER TICKS

| TEST DAYS | GROUP A1 | GROUP A2 | GROUP B1 | GROUP B2 |
|---|---|---|---|---|
| 5 | 100 | 100 | 100 | 100 |
| 28 | 100 | 91.7 | 84.6 | 100 |
| 29 | 100 | 100 | 100 | 100 |

EXAMPLE II

Mosquito Efficacy

Two dogs from each of Test groups A1, B1 and C1 noted above were selected to participate in the mosquito efficacy portion of the study. Prior to Test Day-1, each dog was sedated and placed in a "Gerber-type" collapsible aluminum mosquito rearing cage, 24 inches×24 inches×24 inches. Approximately 50 unfed female mosquitoes were released into each cage.

sedated and placed into the "Gerber-type" mosquito cages and had the number of landings in five minutes recorded, followed two hours later by the live and dead mosquito count and fed mosquito counts.

Efficacy for the control and repellency of mosquitoes for Formulation A and B from the previous Example was determined by comparing data collected for mosquito landing rates, mosquito mortality and number of engorged mosquitos at each efficacy evaluation period (Test Days 5, 14, 21, and 28). The efficacy for repellency was calculated as follows:

((Mean number mosquito landings on untreated dogs—Mean number mosquito landings on treated dogs)/Mean number mosquito landings on untreated dogs)× 100.

The efficacy for the insecticidal activity was calculated as follows:

((Mean number live mosquitos on untreated dogs—Mean number of live mosquitos on treated dogs)/Mean number of live mosquitoes on untreated dogs)×100.

The efficacy for preventing the taking of blood from the dogs by the mosquitos was calculated as follows:

((Mean number of blood fed mosquitoes from untreated dogs—Mean number of blood fed mosquitoes from treated dogs)/Mean number of blood fed mosquitoes from untreated dogs)×100.

The results of the mosquito efficacy tests are reported in Table 4.

SUMMARY OF RESULTS FOR EXAMPLE 2

Formulation A was more effective than Formulation B in reducing mosquito landings on dogs through Test Day 21. In general both products were equally efficacious in causing mosquito mortality and in reducing mosquito feedings.

TABLE 4

OVERALL PERCENT (%) EFFICACY AGAINST MOSQUITOES

| GROUP | TEST DAY | PERCENT REDUCTION LANDINGS | PERCENT MORTALITY | PERCENT REDUCTION FEEDING |
|---|---|---|---|---|
| A1 | 5 | 56.0 | 97.2 | 100 |
| B1 | 5 | 26.7 | 100 | 100 |
| A1 | 14 | 13.5 | 100 | 91.9 |
| B1 | 14 | 0 | 100 | 100 |
| A1 | 21 | 14.6 | 100 | 100 |
| B1 | 21 | 0 | 100 | 78.5 |
| A1 | 28 | 0 | 51.9 | 90.9 |
| B1 | 28 | 0 | 100 | 100 |

It is to be understood that while certain forms of the present invention have been illustrated and described herein, it is not to be limited to the specific compositions and methods described.

What is claimed and desired to be secured by Letters Patent is as follows:

1. A method of combating ectoparasites on warm-blooded animals comprising simultaneously externally applying as a spot application and without a time release carrier to said animals a growth regulating effective amount of a pour on enhanced formulation including an amount in a range from about 5% percent to about 50% by weight pyriproxyfen and an ectoparasiticidic effective amount of an ectoparasiticide for adult ectoparasites comprising permethrin in an amount in a range from about 5% to about 50% by weight wherein said enhanced formulation is effective at least over a three month period.

2. The method as disclosed in claim 1 wherein the formulation further includes about 10% by weight mineral oil.

3. The method as disclosed in claim 2 wherein the formulation further includes about 30% by weight D-Limonene.

4. A pour on external spot treatment composition without a time release carrier for use in combating ectoparasites of warm-blooded animals over at least a three month period comprising an enhanced formulation of:

(a) about 5% to about 50% by weight pyriproxyfen;
(b) about 5% to about 50% by weight permethrin;
(c) about 1% to about 30% by weight mineral oil; and
(d) about 10% to about 50% by weight D-Limonene.

5. The composition according to claim 4 having:

(a) about 5% by weight pyriproxyfen;
(b) about 45% by weight permethrin;
(c) about 10% by weight mineral oil; and
(d) about 30% by weight D-Limonene.

\* \* \* \* \*